US009835579B2

(12) United States Patent
Sato

(10) Patent No.: US 9,835,579 B2
(45) Date of Patent: Dec. 5, 2017

(54) ANALYTICAL DEVICE, METHOD FOR MANUFACTURING THE SAME, AND MEASURING APPARATUS USING THE SAME

(71) Applicant: ARKRAY, Inc., Kyoto (JP)

(72) Inventor: Yoshiharu Sato, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 354 days.

(21) Appl. No.: 14/264,187

(22) Filed: Apr. 29, 2014

(65) Prior Publication Data

US 2014/0326601 A1 Nov. 6, 2014

(30) Foreign Application Priority Data

May 2, 2013 (JP) ................................. 2013-097066
Apr. 18, 2014 (JP) ................................. 2014-086657

(51) Int. Cl.
*G01N 27/327* (2006.01)
*G01N 33/543* (2006.01)

(52) U.S. Cl.
CPC ..... *G01N 27/3274* (2013.01); *G01N 33/5438* (2013.01); *Y10T 29/49124* (2015.01)

(58) Field of Classification Search
CPC ................................................ G01N 24/3274
See application file for complete search history.

(56) References Cited

U.S. PATENT DOCUMENTS 5,705,397 A 1/1998 Bunce
2011/0139634 A1 6/2011 Chou et al.
2012/0193228 A1 8/2012 Hsu

FOREIGN PATENT DOCUMENTS

KR 10-2007-0022195 A 2/2007
WO 2005/045414 A1 5/2005

OTHER PUBLICATIONS

Extended European Search Report issued in corresponding European Patent Application No. 14166162.9 dated Aug. 4, 2014.
Office Action issued in corresponding Korean Patent Application No. 10-2014-0052316 dated Dec. 26, 2016.

*Primary Examiner* — Sean E Conley
*Assistant Examiner* — Matthew Krcha
(74) *Attorney, Agent, or Firm* — Morgan, Lewis & Bockius LLP

(57) ABSTRACT

Provided are an analytical device comprising a pair of hematocrit electrodes (first pair of electrodes) and a pair of glucose electrodes (second pair of electrodes) that allows a sample to sufficiently reach as far as the second pair of electrodes that are provided on a downstream side in a flow path, a method for manufacturing the analytical device, and a measuring apparatus using the analytical device.

18 Claims, 11 Drawing Sheets

ANALYTICAL DEVICE, METHOD FOR MANUFACTURING THE SAME, AND MEASURING APPARATUS USING THE SAME

BACKGROUND OF THE INVENTION

1. Field of the Invention

The present invention relates to an analytical device for analyzing a sample such as blood, more particularly an analytical device capable of performing hematocrit correction, as well as a method for manufacturing the analytical device and a measuring apparatus using the analytical device.

2. Description of Related Art

In recent years, medical measuring apparatuses, as typified by blood glucose meters such as portable blood glucose monitoring (BGM) devices and meters for self-monitoring of blood glucose (SMBG), can be used by patients to measure a sample (specimen) such as blood and manage the measurement result (data) by themselves. Specifically, with respect to, for example, the treatment of diabetes, it is crucial to inhibit the onset and the progress of complications by controlling the blood glucose level. Therefore, self-monitoring and management of the blood glucose level by the patients themselves are indispensable.

Also, blood glucose meters as described above are required to provide accurate measurement of the blood glucose level. In order to meet this demand, analytical devices capable of performing hematocrit correction and blood glucose meters (measuring apparatuses) using those analytical devices have been developed and put to practical use.

For example, US 2011/0139634 proposes a biosensor strip, which is an analytical device, in which a pair of glucose electrodes for measurement of glucose and a pair of hematocrit electrodes for hematocrit correction are provided. That is to say, this conventional analytical device is capable of accurately detecting blood glucose levels by correcting the glucose level (blood glucose level) that is detected by the glucose electrodes with the hematocrit value that is detected by the hematocrit electrodes.

Also, in this conventional analytical device, the pair of hematocrit electrodes and the pair of glucose electrodes are sequentially arranged in this order from an upstream side (introduction hole side) in a blood flow path. A reagent is placed on the pair of glucose electrodes, so that the glucose level can be detected by means of the reagent. The reagent is provided on the pair of glucose electrodes by dropping the reagent onto the pair of glucose electrodes and then solidifying the reagent.

Also, in this conventional analytical device, a separated element is provided in order to prevent interference between the reaction with blood at the pair of hematocrit electrodes and the reaction with blood at the pair of glucose electrodes. Specifically, in this conventional analytical device, the separated element is formed corresponding to and in the middle of the pair of hematocrit electrodes and the pair of glucose electrodes in the blood flow path without coming into contact with the two pairs of electrodes so that a region in which the pair of hematocrit electrodes are provided and a region in which the pair of glucose electrodes are provided are separated from each other.

Also, in this conventional analytical device, the separated element is formed by a spacer, and two insulation layers are provided such that the spacer is sandwiched therebetween, so that blood from the introduction hole side can reach the side of the pair of glucose electrodes. Specifically, in this conventional analytical device, an opening constituting the blood flow path is formed in each of the two insulation layers, and the separated element is disposed between the two openings. This configuration enables blood to reach the side of the pair of glucose electrodes.

SUMMARY OF THE INVENTION

An object of the disclosure of the present application is to provide an analytical device that allows a sample to sufficiently reach as far as a second pair of electrodes that are provided on a downstream side in a flow path, a method for manufacturing the analytical device, and a measuring apparatus using the analytical device.

Also, an object of the disclosure of the present application is to provide an analytical device that allows a sufficient amount of reagent to be dropped on a pair of electrodes, a method for manufacturing the analytical device, and a measuring apparatus using the analytical device.

In order to achieve these objectives, an analytical device according to the disclosure of the present application includes:
   a substrate;
   a defining element defining a flow path of a sample;
   a first pair of electrodes formed on the substrate and located on an upstream side in the flow path;
   a second pair of electrodes formed on the substrate and located on a downstream side in the flow path; and
   a dropped reagent restricting element formed between the downstream end portion of the first pair of electrodes and the upstream end portion of the second pair of electrodes in the flow path, the dropped reagent restricting element restricting movement of a dropped reagent,
   wherein in the flow path, the dropped reagent restricting element and a gap are provided in a crosswise direction that crosses an inflow direction of the sample.

Also, an analytical device according to the disclosure of the present application includes:
   a substrate;
   a defining element defining a flow path of a sample;
   a first pair of electrodes formed on the substrate and located on an upstream side in the flow path;
   a second pair of electrodes formed on the substrate and located on a downstream side in the flow path; and
   a dropped reagent restricting element formed between the downstream end portion of the first pair of electrodes and the upstream end portion of the second pair of electrodes in the flow path, the dropped reagent restricting element restricting movement of a dropped reagent,
   wherein the dropped reagent restricting element is formed on either of one pair of the first pair of electrodes and the second pair of electrodes.

Also, a method for manufacturing an analytical device according to the disclosure of the present application is a method for manufacturing an analytical device including a substrate, a defining element defining a flow path of a sample, a first pair of electrodes, and a second pair of electrodes, the method including:
   a first electrode pair forming step of forming the first pair of electrodes on an upstream side in the flow path on the substrate;
   a second electrode pair forming step of forming the second pair of electrodes on a downstream side in the flow path on the substrate; and
   a dropped reagent restricting element forming step of forming a dropped reagent restricting element between the downstream end portion of the first pair of electrodes and the upstream end portion of the second pair of electrodes in the flow path such that a gap is created in a crosswise direction that crosses an inflow direction of the sample, the dropped reagent restricting element restricting movement of a dropped reagent.

The disclosure of the present application provides for an analytical device that allows the sample to sufficiently reach as far as the second pair of electrodes that are provided on the downstream side in the flow path, a method for manufacturing the analytical device, and a measuring apparatus using the analytical device.

The disclosure of the present application also provides for an analytical device that allows a sufficient amount of reagent to be dropped on a pair of electrodes, a method for manufacturing the analytical device, and a measuring apparatus using the analytical device.

BRIEF DESCRIPTION OF THE DRAWINGS

FIGS. 6A and 6B illustrate a series of manufacturing steps.

DETAILED DESCRIPTION OF THE INVENTION

Figure 1:
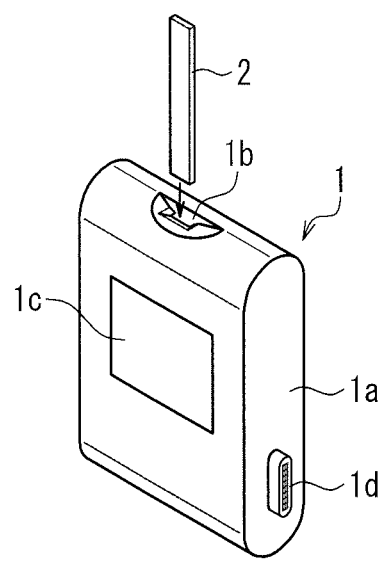
FIG. 1 is a perspective view for explaining an analytical device according to a first embodiment of the invention and a blood glucose meter using the analytical device.

In analytical devices such as biosensor strips, in order to prevent a (dropped) reagent that is dropped on glucose electrodes from moving to the side of hematocrit electrodes during manufacturing, a dropped reagent restricting element of some type is required.

Thus, in analytical devices as described above, a separated element (e.g., a dropped reagent restricting element) is provided such that a region in which a pair of hematocrit electrodes (e.g., a first pair of electrodes) are provided and a region in which a pair of glucose electrodes (e.g., a second pair of electrodes) are provided are separated from each other. In this case, the problem may arise that the analytical devices do not allow blood (i.e., the sample) to sufficiently reach the pair of glucose electrodes that are provided on the downstream side in the flow path depending on the thicknesses of the above-described two insulation layers, the sizes of the above-described openings, etc.

Also, in the analytical devices, if the separated element is placed in the middle position between the pair of hematocrit electrodes and the pair of glucose electrodes, there are instances where the region in which the pair of glucose electrodes is provided is small, resulting in the problem that a sufficient amount of (dropped) reagent cannot be dropped thereon.

Note that in order to drop a sufficient amount of reagent, increasing the distance between the pair of hematocrit electrodes and the pair of glucose electrodes or increasing the size of the entire flow path is conceivable. However, if such a configuration is employed, the volume of the flow path increases, leading to another problem such that the patients (users) may be adversely affected. More specifically, the increase in the volume of the flow path necessitates taking a large amount of blood, that is, a specimen from a patient, which can be painful for the patient.

Therefore, with the foregoing problems in mind, an object of embodiments of the invention is to provide an analytical device that allows the sample to sufficiently reach as far as the second pair of electrodes that are provided on the downstream side in the flow path, a method for manufacturing the analytical device, and a measuring apparatus using the analytical device.

Also, an object of embodiments of the invention is to provide an analytical device that allows a sufficient amount of reagent to be dropped on a pair of electrodes, a method for manufacturing the analytical device, and a measuring apparatus using the analytical device.

In order to achieve these objectives, an analytical device according to an embodiment of the invention includes:
  a substrate;
  a defining element defining a flow path of a sample;
  a first pair of electrodes formed on the substrate and located in the flow path;
  a second pair of electrodes formed on the substrate and located downstream of the first pair of electrodes in the flow path; and
  a dropped reagent restricting element formed between a downstream end portion of the first pair of electrodes and an upstream end portion of the second pair of electrodes in the flow path, the dropped reagent restricting element restricting movement of a dropped reagent,
  wherein in the flow path, the dropped reagent restricting element and a gap are provided in a crosswise direction that crosses an inflow direction of the sample.

In the analytical device configured as described above, the dropped reagent restricting element is formed between the downstream end portion of the first pair of electrodes and the upstream end portion of the second pair of electrodes in the flow path. Furthermore, in the flow path, the dropped reagent restricting elements and the gap are provided in the crosswise direction that crosses the inflow direction of the sample. Therefore, unlike the above-described conventional example, the sample is allowed to sufficiently reach as far as the second pair of electrodes that are provided on the downstream side in the flow path.

In the analytical device, it is preferable that the dropped reagent restricting element is formed on either one pair of the first pair of electrodes and the second pair of electrodes.

In this case, a sufficient amount of reagent can be dropped on the other pair of the first and second pairs of electrodes. Also, the dropped reagent restricting element can reliably restrict the movement of the dropped reagent.

In the analytical device, it is also possible that the dropped reagent is dropped on the second pair of electrodes, and
 the dropped reagent restricting element is formed on the first pair of electrodes.

In this case, a sufficient amount of reagent can be dropped on the second pair of electrodes. Also, the dropped reagent restricting element can reliably restrict the movement of the dropped reagent.

An analytical device according to an embodiment of the invention includes:
 a substrate;
 a defining element defining a flow path of a sample;
 a first pair of electrodes formed on the substrate and located in the flow path;
 a second pair of electrodes formed on the substrate and located downstream of the first pair of electrodes in the flow path; and
 a dropped reagent restricting element formed between the downstream end portion of the first pair of electrodes and the upstream end portion of the second pair of electrodes in the flow path, the dropped reagent restricting element restricting movement of a dropped reagent,
 wherein the dropped reagent restricting element is formed on either of one pair of the first pair of electrodes and the second pair of electrodes.

In the analytical device configured as described above, the dropped reagent restricting element is formed between the downstream end portion of the first pair of electrodes and the upstream end portion of the second pair of electrodes in the flow path. Furthermore, the dropped reagent restricting element is formed on either of one pair of the first pair of electrodes and the second pair of electrodes. Therefore, unlike the above-described conventional example, a sufficient amount of reagent can be dropped on the other pair of the first pair of electrodes and the second pair of electrodes. Also, the dropped reagent restricting element is able to reliably restrict the movement of the dropped reagent.

In the analytical device, it is preferable that the dropped reagent restricting element is provided in a central portion with respect to the crosswise direction that crosses the inflow direction of the sample.

In this case, the movement of the dropped reagent can be more reliably restricted.

In the analytical device, it is preferable that the dropped reagent restricting element is formed integrally with a portion of the defining element.

In this case, it is possible to easily construct an analytical device having a small number of components and a simple structure.

In the analytical device, it is preferable that the dropped reagent restricting element is an insulator.

In this case, it is possible to easily construct an analytical device that is easy to manufacture.

It is preferable that the analytical device further includes an opposing substrate that is provided opposite the substrate and an adhesive layer for making the substrate and the opposing substrate adhere to each other, and
 the defining element includes an insulator provided on the substrate, the adhesive layer, and the opposing substrate.

In this case, it is possible to easily construct a low-cost analytical device having a simple structure and a reduced thickness.

In the analytical device, it is preferable that a vent communicating with the flow path is provided in the opposing substrate.

In this case, it is possible to make the sample smoothly flow into the flow path.

Also, a method for manufacturing an analytical device according to an embodiment of the invention is a method for manufacturing an analytical device including a substrate, a defining element defining a flow path of a sample, a first pair of electrodes, and a second pair of electrodes, the method including:
 a first electrode pair forming step of forming the first pair of electrodes in the flow path on the substrate;
 a second electrode pair forming step of forming the second pair of electrodes downstream of the first pair of electrodes in the flow path on the substrate; and
 a dropped reagent restricting element forming step of forming a dropped reagent restricting element between the downstream end portion of the first pair of electrodes and an upstream end portion of the second pair of electrodes in the flow path such that a gap is created in a crosswise direction that crosses an inflow direction of the sample, the dropped reagent restricting element restricting movement of a dropped reagent.

According to the method for manufacturing an analytical device, the method being configured as described above, the dropped reagent restricting element, which restricts the movement of the dropped reagent, is formed between the downstream end portion of the first pair of electrodes and the upstream end portion of the second pair of electrodes in the flow path by the dropped reagent restricting element forming step such that the gap is created in the crosswise direction that crosses the inflow direction of the sample. Therefore, it is possible to manufacture an analytical device that allows the sample to sufficiently reach as far as the second pair of electrodes that are provided on the downstream side in the flow path.

In the method for manufacturing an analytical device, it is preferable that in the dropped reagent restricting element forming step, the dropped reagent restricting element is formed on either of one pair of the first pair of electrodes and the second pair of electrodes.

In this case, it is possible to manufacture an analytical device that allows a sufficient amount of reagent to be dropped on the other pair of the first pair of electrodes and the second pair of electrodes.

Also, a measuring apparatus according to an embodiment of the invention uses any of the above-described analytical devices.

According to the measuring apparatus configured as described above, the use of the analytical device that allows the sample to sufficiently reach as far as the second pair of electrodes that are provided on the downstream side in the flow path makes it possible to easily construct a measuring apparatus capable of performing an accurate measurement with respect to the sample.

Hereinafter, preferred embodiments exemplifying an analytical device, a method for manufacturing the analytical device, and a measuring apparatus using the analytical device according to the invention will be described with reference to the drawings. Note that in the following descriptions, a case where the invention is applied to a blood glucose meter is taken as an example. Also, the dimensions of constituent members shown in the drawings are exemplary representations of the actual dimensions of the constituent members, the actual dimensional ratios of the constituent members, etc.

First Embodiment

FIG. 1 is a perspective view for explaining an analytical device according to a first embodiment of the invention and a blood glucose meter using the analytical device. Referring to FIG. 1, in this embodiment, a portable blood glucose meter 1 serving as a measuring apparatus, and an analytical device 2 of this embodiment that is configured to be removably attached to the blood glucose meter 1 are provided. The analytical device 2 is adapted so that blood (a sample) of a patient can be deposited on (introduced into) the analytical device 2. The analytical device 2 is configured to have the function of a (bio)sensor for detecting the blood glucose level (glucose level) in blood.

The blood glucose meter 1 includes a main body 1a, and an insertion port 1b into which the analytical device 2 having the shape of a rectangular strip can be inserted is formed in the main body 1a. Also, a control unit (not shown) that may be configured by a microprocessor, for example, and that controls various units of the blood glucose meter 1 is provided in the main body 1a. The main body 1a also includes a measurement unit that supplies a predetermined voltage signal to the analytical device 2, receives a voltage signal indicating the measurement result from the analytical device 2, performs an analog-to-digital conversion of the received voltage signal, and generates measurement data indicating the measured value, and a recording unit that records the measurement data obtained by the measurement unit (the measurement unit and the recording unit are not shown in the drawings). The above-described control unit causes the measurement data obtained by the measurement unit to be recorded in the recording unit in association with the measuring time, a patient ID, etc.

Also, a display screen 1c on which the measurement data is displayed and a connector 1d for data communication with an external apparatus are provided on the main body 1a. The connector 1d is configured to send/receive data such as the measurement data, measuring time, patient ID, etc. to/from a portable apparatus such as a smartphone, a personal computer, or the like serving as the external apparatus. That is to say, the blood glucose meter 1 is configured to be able to transfer the measurement data and the measuring time to the external apparatus via the connector 1d, and receive the patient ID etc. from the external apparatus via the connector 1d and associate the received patient ID etc. with the measurement data etc.

Note that instead of the configuration described above, it is also possible to adopt a configuration in which the measurement unit is provided in an end portion of the analytical device 2, and the measurement data is generated by the analytical device 2. Moreover, the main body 1a of the blood glucose meter 1 may also be equipped with a user interface including an input unit such as a keypad or a touch panel through which the user such as a patient inputs data.

Next, the analytical device 2 of this embodiment will be specifically described with reference to FIGS. 2 to 5.

Figure 2:
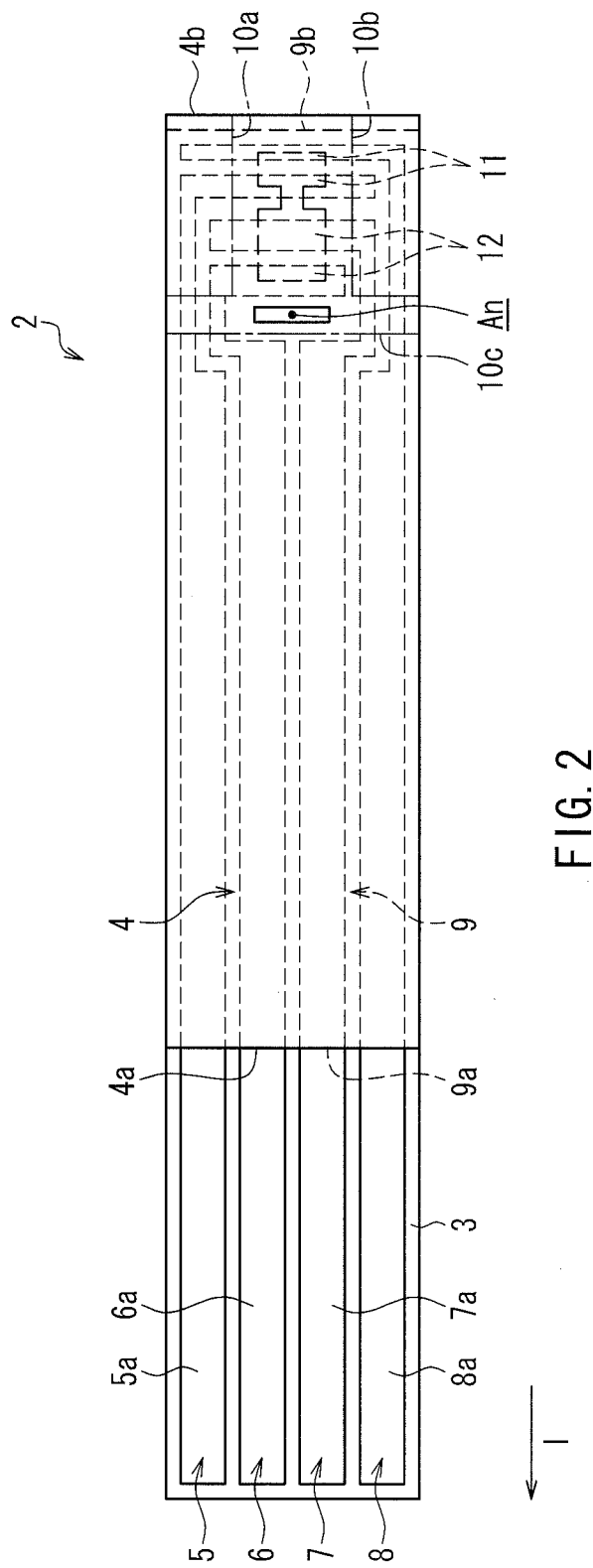
FIG. 2 is a plan view for explaining the analytical device shown in FIG. 1.
Figure 3:
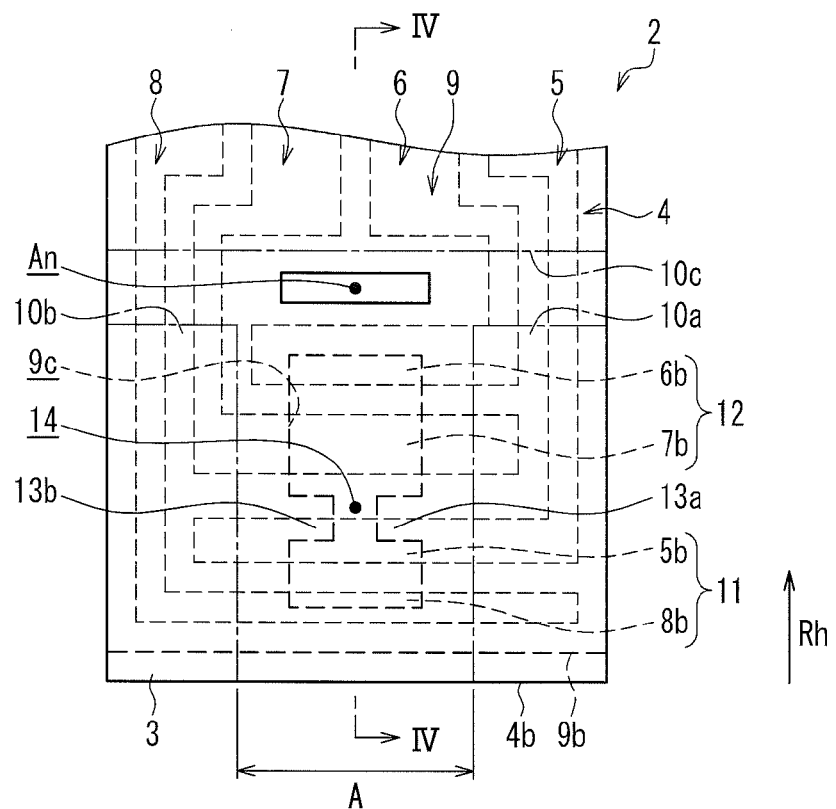
FIG. 3 is an enlarged plan view for explaining the configuration of a portion of the analytical device on the side of a blood introduction hole.
Figure 4:
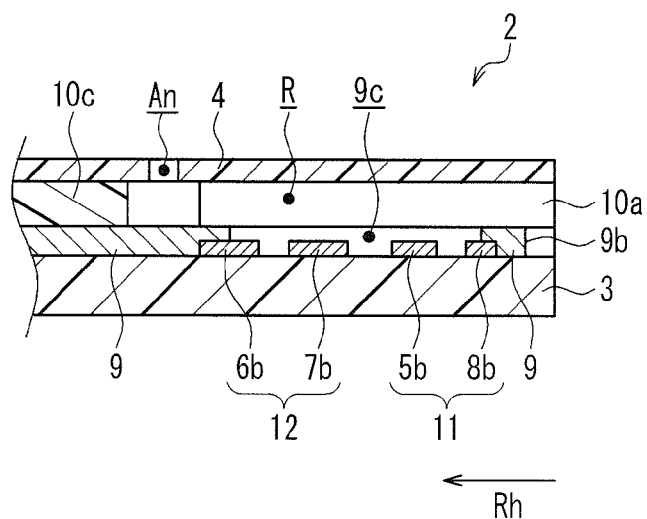
FIG. 4 is a cross-sectional view taken along line IV-IV in FIG. 3.
Figure 5:
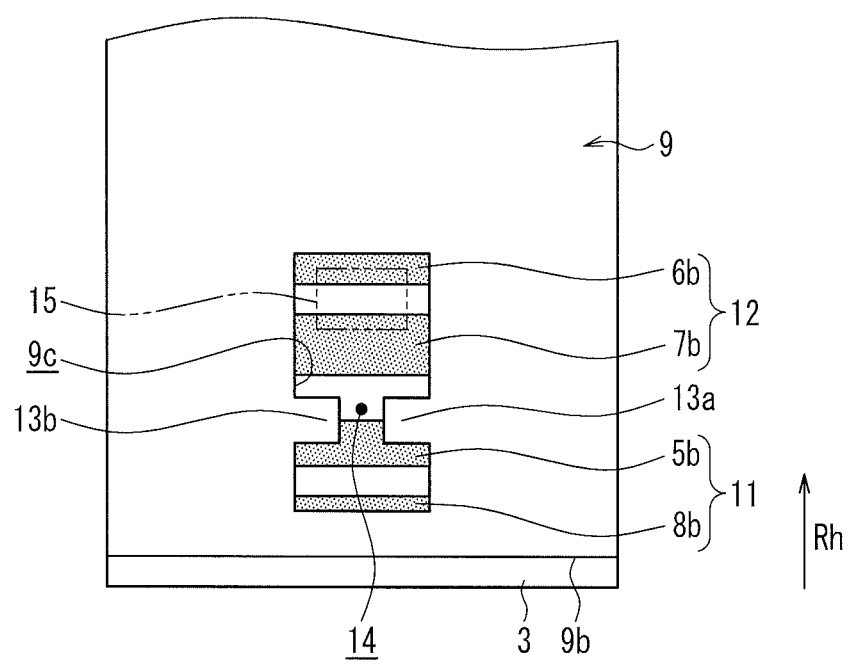
FIG. 5 is an enlarged plan view for explaining the configuration of a relevant portion of the analytical device.

FIG. 2 is a plan view for explaining the analytical device shown in FIG. 1. FIG. 3 is an enlarged plan view for explaining the configuration of a portion of the above-described analytical device on the side of a blood introduction hole. FIG. 4 is a cross-sectional view taken along line IV-IV in FIG. 3. FIG. 5 is an enlarged plan view for explaining the configuration of a relevant portion of the above-described analytical device.

Referring to FIG. 2, in the analytical device 2 of this embodiment, a substrate 3 and an opposing substrate 4 that is provided opposite the substrate 3 with a resist ink 9 being interposed between the two substrates are provided. As will be described in detail later, an introduction hole from which blood is introduced is provided at a right end portion of this analytical device 2 in FIG. 2. Moreover, the analytical device 2 is adapted to be inserted into the insertion port 1b (FIG. 1) of the blood glucose meter 1 in the direction of arrow "I" in FIG. 2.

For example, a hydrophobic synthetic resin may be used for the substrate 3. Four signal lines 5, 6, 7, and 8 are formed on the substrate 3. For example, carbon ink may be used for these signal lines 5, 6, 7, and 8. The signal lines 5, 6, 7, and 8 are formed in a predetermined pattern on the substrate 3 by screen printing, for example. Specifically, the signal lines 5, 6, 7, and 8 have linear wiring portions 5a, 6a, 7a, and 8a having the same width and electrode portions 5b, 6b, 7b, and 8b (FIG. 3) that are bent at right angles to the respective wiring portions 5a, 6a, 7a, and 8a.

Note that instead of the configuration described above, the signal lines 5, 6, 7, and 8 may also be formed using a thin metal film, for example.

Also, in the analytical device 2, as shown in FIG. 2, a left end portion (insertion portion) of the substrate 3 is not covered by the opposing substrate 4 and the resist ink 9, so that left end portions of the above-described wiring portions 5a, 6a, 7a, and 8a are exposed. The analytical device 2 is thus configured such that when the analytical device 2 is inserted into the insertion port 1b, the left end portions of the respective wiring portions 5a, 6a, 7a, and 8a are connected to a connecting unit (not shown) provided inside the main body 1a (FIG. 1) of the blood glucose meter 1, allowing the analytical device 2 to exchange voltage signals with the blood glucose meter 1.

Also, in the analytical device 2, as shown in FIG. 2, a pair of hematocrit electrodes 11 and a pair of glucose electrodes 12 are provided in a right end portion (sample inlet portion) of the analytical device 2, so that blood introduced into the analytical device 2 from the introduction hole travels along the flow path, which will be described later, and reaches the hematocrit electrodes 11 and the glucose electrodes 12.

For example, a hydrophilic synthetic resin may be used for the opposing substrate 4. A left end (insertion-side end portion) 4a of the opposing substrate 4 is positioned such that the left end portions of the respective wiring portions 5a, 6a, 7a, and 8a are exposed as described above. On the other hand, a right end (sample inlet-side end portion) 4b of the opposing substrate 4 is configured so as to coincide with a right end of the analytical device 2 (i.e., right end of the substrate 3). The hydrophilicity of the opposing substrate 4 allows blood traveling along the above-described flow path to readily reach the pair of glucose electrodes 12, which are provided on the downstream side with respect to an inflow direction of the blood. Furthermore, a vent An communicating with the flow path is formed in the opposing substrate 4, so that blood (sample) can smoothly flow into the flow path.

For example, an insulator such as thermosetting ink may be used for the resist ink 9. The resist ink 9 is formed in a predetermined pattern on the substrate 3 and on the signal lines 5, 6, 7, and 8 by screen printing, for example. More specifically, a left end 9a of the resist ink 9 is configured so as to coincide with the left end 4a of the opposing substrate 4. On the other hand, as shown in FIG. 2, a right end 9b of the resist ink 9 is configured so as to be located slightly to the left of the right end 4b of the opposing substrate 4. Since an insulator is used for the resist ink 9, the signal lines 5, 6, 7, and 8 are not adversely affected, and hence the measurement accuracy are not adversely affected.

Rectangular double-sided adhesive tapes 10a, 10b, and 10c are provided on the resist ink 9 such that the double-sided adhesive tapes 10a, 10b, and 10c are interposed between the resist ink 9 and the opposing substrate 4. The double-sided adhesive tapes 10a, 10b, and 10c serve as an adhesive layer for making the substrate 3 and the opposing substrate 4 adhere to each other and is adapted to make the substrate 3 and the opposing substrate 4 adhere to each other via the resist ink 9, which is formed on the substrate 3. Note that a double-sided adhesive tape having the same width as the substrate 3, the opposing substrate 4, and the resist ink 9 is used as the double-sided adhesive tape 10c, and one end (left end in FIG. 2) of the double-sided adhesive tape 10c coincides with the left end 4a of the opposing substrate 4 and the left end 9a of the resist ink 9. The aforementioned vent An is formed in the opposing substrate 4 at a position between the other end (right end in FIG. 2) of the double-sided adhesive tape 10c and the double-sided adhesive tapes 10a and 10b.

Note that instead of the configuration described above, the resist ink 9 may also be formed using an ultraviolet-curing resin, for example.

In the analytical device 2 of this embodiment, as indicated by "A" in FIG. 3, the blood introduction hole is formed at a lower end portion of the analytical device 2. The opening of this introduction hole is defined by the substrate 3, the opposing substrate 4, the resist ink 9, and the double-sided adhesive tapes 10a and 10b. A blood flow path R is formed inside the analytical device 2, extending from the opening toward the upper side in FIG. 3 (see also FIG. 4). Blood flows into this flow path R from the introduction hole in the inflow direction indicted by "Rh" in FIGS. 3 and 4 by capillary action. Note that in order to facilitate this capillary action, the above-described vent An is formed in the opposing substrate 4.

That is to say, in the analytical device 2 of this embodiment, the substrate 3, the opposing substrate 4, the resist ink (insulator) 9, and the double-sided adhesive tapes (adhesive layer) 10a, 10b, and 10c constitute a defining element that defines the flow path R of blood (sample). The length of the flow path R may be set at, for example, 1.1 to 10 mm, 1.5 to 4.5 mm, or 2 to 4 mm. The width of the flow path R may be set at, for example, 1 to 10 mm, 2 to 3.5 mm, or 1.5 to 2.5 mm. Furthermore, the capacity of the flow path R may be set at, for example, 0.1 to 10 μL, 0.15 to 0.5 μL, or 0.25 to 0.35 μL.

Also, in the flow path R, as shown in FIGS. 3 to 5, a cutout portion 9c is formed in the resist ink 9. Also, in the flow path R, the pair of hematocrit electrodes 11, which are a first pair of electrodes, are provided so as to be located on an upstream side (introduction hole side) in the flow path R, and the pair of glucose electrodes 12, which are a second pair of electrodes, are provided so as to be located downstream of the pair of hematocrit electrodes 11.

Specifically, the pair of hematocrit electrodes 11 are substantially constituted by those portions of the electrode portions 5b and 8b that are exposed in the cutout portion 9c. At the pair of hematocrit electrodes 11, in a state in which the above-described exposed portions of the electrode portions 5b and 8b are in contact with blood, a voltage signal based on an alternating voltage (AC) or a direct voltage (DC) is supplied to the signal lines 5 and 8, and thus the hematocrit value is detected by the blood glucose meter 1.

The pair of glucose electrodes 12 are substantially constituted by those portions of the electrode portions 6b and 7b that are exposed in the cutout portion 9c. Also, a solidified dropped reagent 15 is placed on the pair of glucose electrodes 12 as shown by a chain double-dashed line in FIG. 5. At the pair of glucose electrodes 12, in a state in which the above-described exposed portions of the electrode portions 6b and 7b and the dropped reagent 15 are in contact with blood, and the blood reacts with the dropped reagent 15, a voltage signal based on an alternating voltage (AC) or a direct voltage (DC) is supplied to the signal lines 6 and 7, and thus, the glucose level (blood glucose level) is detected by the blood glucose meter 1. In the measuring apparatus 1, the detected glucose level is corrected using the detected hematocrit value, and the corrected glucose level is treated as measurement data.

In the manufacturing process of the analytical device 2, before the opposing substrate 4 and the substrate 3 are bonded together, the reagent 15 in a liquid state is dropped on the pair of glucose electrodes 12 by an apparatus for ejecting a fixed amount of liquid, such as a dispenser, and the dropped reagent 15 is dried and thus solidified on the glucose electrodes 12.

Also, in the flow path R, as illustrated in FIG. 5, dropped reagent restricting elements 13a and 13b that restrict the movement of the dropped reagent 15 in the liquid state are provided between a downstream end portion of the pair of hematocrit electrodes 11 and an upstream end portion of the pair of glucose electrodes 12. The dropped reagent restricting elements 13a and 13b are formed integrally with the resist ink (defining element) 9. As shown in FIG. 5, the dropped reagent restricting elements 13a and 13b are formed on the electrode portion 5b of one of the pair of hematocrit electrodes 11. More specifically, a portion of each of the dropped reagent restricting elements 13a and 13b is provided so as to be overlaid on a portion of the electrode portion 5b, and the other portion of each of the dropped reagent restricting elements 13a and 13b is provided between the downstream end portion of the pair of hematocrit electrodes 11 and the upstream end portion of the pair of glucose electrodes 12.

Also, in the flow path R, as illustrated in FIG. 5, the dropped reagent restricting elements 13a and 13b and a gap 14 are provided in a crosswise direction that crosses the inflow direction Rh of blood (e.g., orthogonal direction that is orthogonal to the inflow direction Rh). That is to say, in the flow path R, the gap 14 is formed between the two dropped reagent restricting elements 13a and 13b.

Next, a method for manufacturing the analytical device 2 of this embodiment will be specifically described using FIG. 6. Note that in the following description, steps of forming the dropped reagent restricting elements 13a and 13b and the gap 14 after forming the signal lines 5, 6, 7, and 8 on the substrate 3 will be mainly described.

Figure 6A:
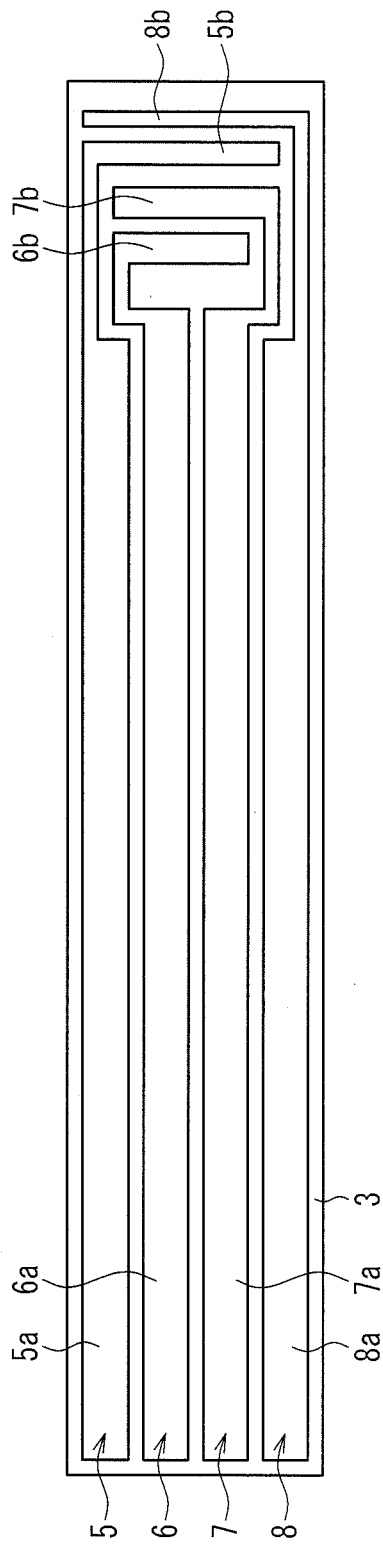
FIGS. 6A and 6B are diagrams for explaining a method for manufacturing the analytical device, where
Figure 6B:
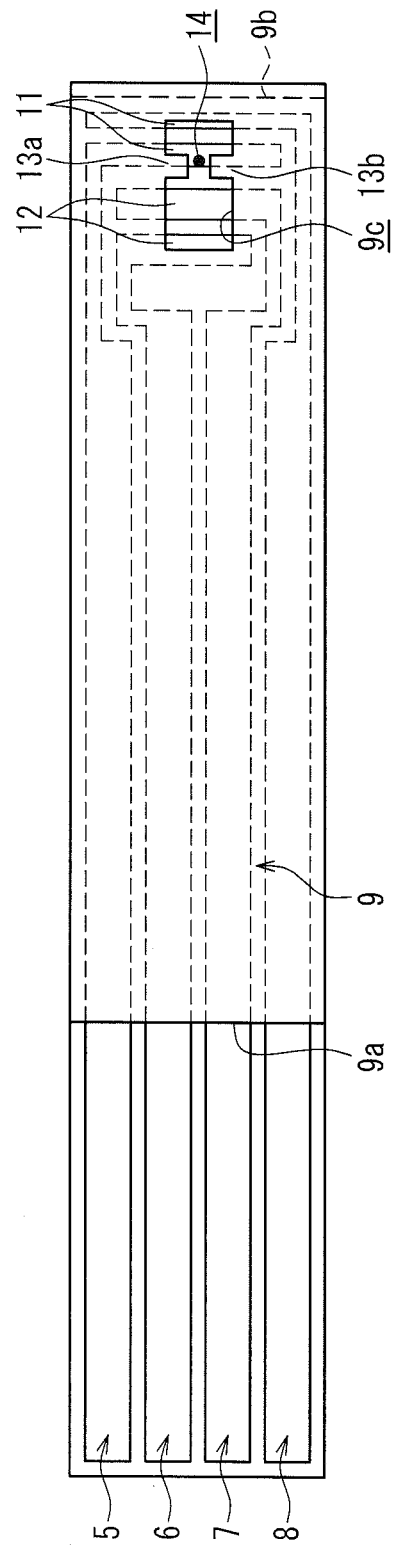

FIGS. 6A and 6B are diagrams for explaining a method for manufacturing the analytical device, where FIGS. 6A and 6B illustrate a series of manufacturing steps.

As shown in FIG. 6A, the signal lines 5, 6, 7, and 8 are simultaneously formed on the substrate 3 by screen printing, for example. More specifically, the linear wiring portions 5a, 6a, 7a, and 8a that are parallel to one another and the electrode portions 5b, 6b, 7b, and 8b that are orthogonal to the respective wiring portions 5a, 6a, 7a, and 8a are formed on the substrate 3. Thus, a first electrode pair forming step of forming the pair of hematocrit electrodes (first pair of electrodes) 11 in the flow path R on the substrate 3 and a second electrode pair forming step of forming the pair of glucose electrodes (second pair of electrodes) 12 downstream of the pair of hematocrit electrodes (first pair of electrodes) 11 in the flow path R on the substrate 3 are substantially simultaneously performed.

Note that instead of the configuration described above, a configuration may also be adopted in which either one of the first electrode pair forming step and the second electrode pair forming step is performed prior to the other. Also, instead of the configuration described above, the signal lines 5, 6, 7, and 8 may also be formed on the substrate 3 using other methods such as vacuum deposition and CVD, for example.

Next, as shown in FIG. 6B, the resist ink 9 is formed on the substrate 3 and the signal lines 5, 6, 7, and 8 by screen printing, for example. At this time, the resist ink 9 is patterned such that the left end portions of the wiring portions 5a, 6a, 7a, and 8a are exposed and the cutout portion 9c is formed, as shown in FIG. 6B. The formation of the resist ink 9 completes a dropped reagent restricting element forming step of forming the dropped reagent restricting elements 13a and 13b, which restrict the movement of the dropped reagent 15, such that the gap 14 is created in the flow path R between the downstream end portion of the pair of hematocrit electrodes (first pair of electrodes) 11 and the upstream end portion of the pair of glucose electrodes (second pair of electrodes) 12 in a crosswise direction that crosses the inflow direction Rh of blood (sample). In this dropped reagent restricting element forming step, the dropped reagent restricting elements 13a and 13b are formed on the pair of hematocrit electrodes 11.

Furthermore, the first electrode pair forming step and the second electrode pair forming step are completed simultaneously with the dropped reagent restricting element forming step. That is to say, since the resist ink 9 is provided such that the cutout portion 9c is formed, in the cutout portion 9c, portions of the electrode portions 5b and 8b are exposed and substantially constitute the pair of hematocrit electrodes 11, and portions of the electrode portions 6b and 7b are exposed and substantially constitute the pair of glucose electrodes 12.

After that, the reagent 15 is dropped on the pair of glucose electrodes 12, and then the opposing substrate 4 is placed on the substrate 3 by means of the double-sided adhesive tapes 10a and 10b that are provided on the resist ink 9. The analytical device 2 of this embodiment is thus finished.

In the analytical device 2 of this embodiment configured as described above, the dropped reagent restricting elements 13a and 13b are formed between the downstream end portion of the pair of hematocrit electrodes (first pair of electrodes) 11 and the upstream end portion of the pair of glucose electrodes (second pair of electrodes) 12 in the flow path R. Furthermore, in the analytical device 2 of this embodiment, in the flow path R, the dropped reagent restricting elements 13a and 13b and the gap 14 are provided in the crosswise direction that crosses the inflow direction Rh of blood (sample). Thus, unlike the above-described conventional example, the analytical device 2 of this embodiment allows blood to sufficiently reach as far as the pair of glucose electrodes 12, which are provided on the downstream side in the flow path R.

Also, according to this embodiment, since the dropped reagent restricting elements 13a and 13b are formed on the pair of hematocrit electrodes 11, a sufficient amount of the reagent 15 can be dropped on the pair of glucose electrodes 12. Also, the dropped reagent restricting elements 13a and 13b can reliably restrict the movement of the dropped reagent 15. That is to say, the dropped reagent restricting elements 13a and 13b can reliably suppress the movement of the dropped reagent 15 to the side of the pair of hematocrit electrodes 11.

Also, according to this embodiment, since the dropped reagent restricting elements 13a and 13b are formed integrally with a portion of the resist ink (defining element) 9, it is possible to easily construct an analytical device 2 having a small number of components and a simple structure.

Also, according to this embodiment, since the dropped reagent restricting elements 13a and 13b are made of an insulator, it is possible to easily construct an analytical device 2 that is easy to manufacture.

Also, according to this embodiment, the opposing substrate 4, which is provided opposite the substrate 3, and the double-sided adhesive tapes (adhesive layer) 10a, 10b, and 10c for making the substrate 3 and the opposing substrate 4 adhere to each other are provided, and the defining element includes the resist ink (insulator) 9, which is provided on the substrate 3, the double-sided adhesive tapes 10a, 10b, and 10c, and the opposing substrate 4. Thus, according to this embodiment, it is possible to easily construct a low-cost analytical device 2 having a simple structure and a reduced thickness.

The method for manufacturing the analytical device 2 of this embodiment includes the first electrode pair forming step of forming the pair of hematocrit electrodes (first pair of electrodes) 11 on the substrate 3, the pair of hematocrit electrodes (first pair of electrodes) 11 being provided on the upstream side in the flow path R, the second electrode pair forming step of forming the pair of glucose electrodes (second pair of electrodes) 12 on the substrate 3, the pair of glucose electrodes (second pair of electrodes) 12 being provided on the downstream side in the flow path R, and the dropped reagent restricting element forming step of forming the dropped reagent restricting elements 13a and 13b, which restrict the movement of the dropped reagent 15, such that the gap 14 is created in the crosswise direction that crosses the inflow direction Rh of blood (sample) in the flow path R, the gap 14 being located between the downstream end portion of the pair of hematocrit electrodes 11 and the upstream end portion of the pair of glucose electrodes 12. Thus, according to the method for manufacturing the analytical device 2 of this embodiment, the dropped reagent restricting elements 13a and 13b and the gap 14 are formed between the downstream end portion of the pair of hematocrit electrodes 11 and the upstream end portion of the pair of glucose electrodes 12 in the flow path R by the dropped reagent restricting element forming step. As a result, according to the method for manufacturing the analytical device 2 of this embodiment, it is possible to manufacture an analytical device 2 that allows blood to sufficiently reach as far as the pair of glucose electrodes 12, which are provided on the downstream side in the flow path R.

Also, according to the method for manufacturing the analytical device 2 of this embodiment, since the dropped reagent restricting elements 13a and 13b are formed on the pair of hematocrit electrodes 11 in the dropped reagent restricting element forming step, a sufficient amount of reagent 15 can be dropped on the pair of glucose electrodes 12.

Also, according to the method for manufacturing the analytical device 2 of this embodiment, in the first and second electrode pair forming steps, the pair of hematocrit electrodes 11 and the pair of glucose electrodes 12 are simultaneously formed on the substrate 3 using screen printing. Thus, according to this embodiment, the pair of hematocrit electrodes 11 and the pair of glucose electrodes 12 can be formed with high precision in a short period of time.

Also, according to this embodiment, the use of the analytical device 2 that allows blood (sample) to sufficiently reach as far as the pair of glucose electrodes (second pair of electrodes) 12, which are provided on the downstream side in the flow path R, makes it possible to easily construct a blood glucose meter (measuring apparatus) 1 capable of performing an accurate measurement with respect to the blood.

Second Embodiment

Figure 7:
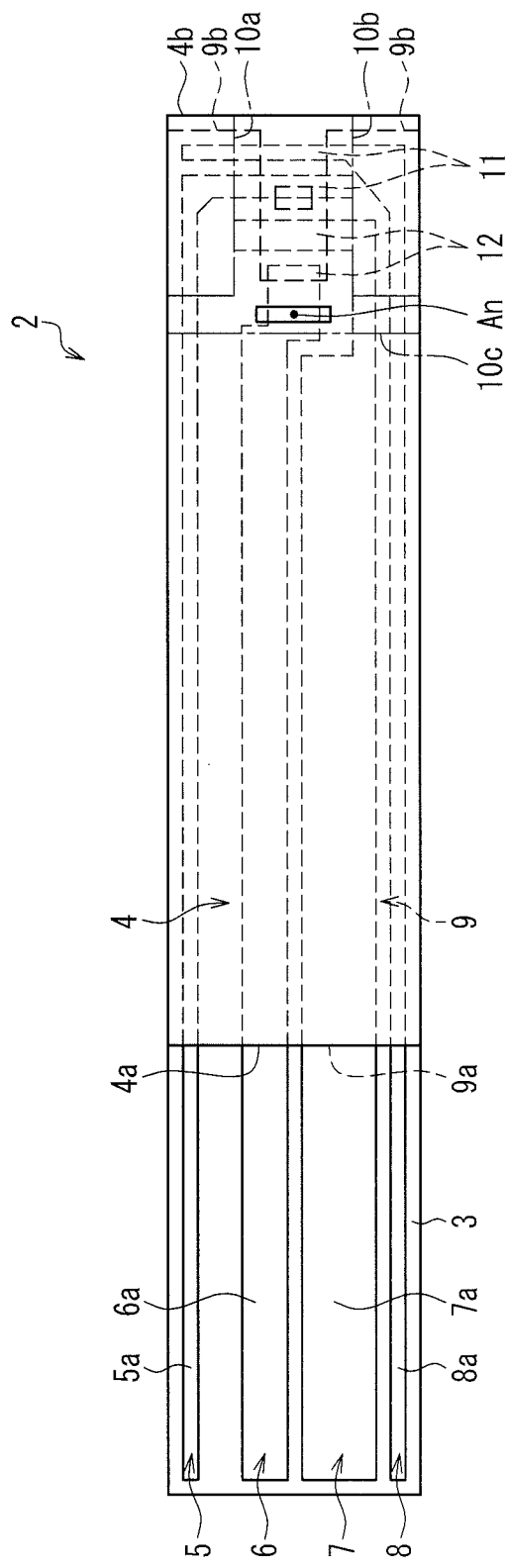
FIG. 7 is a plan view for explaining an analytical device according to a second embodiment of the invention.
Figure 8:
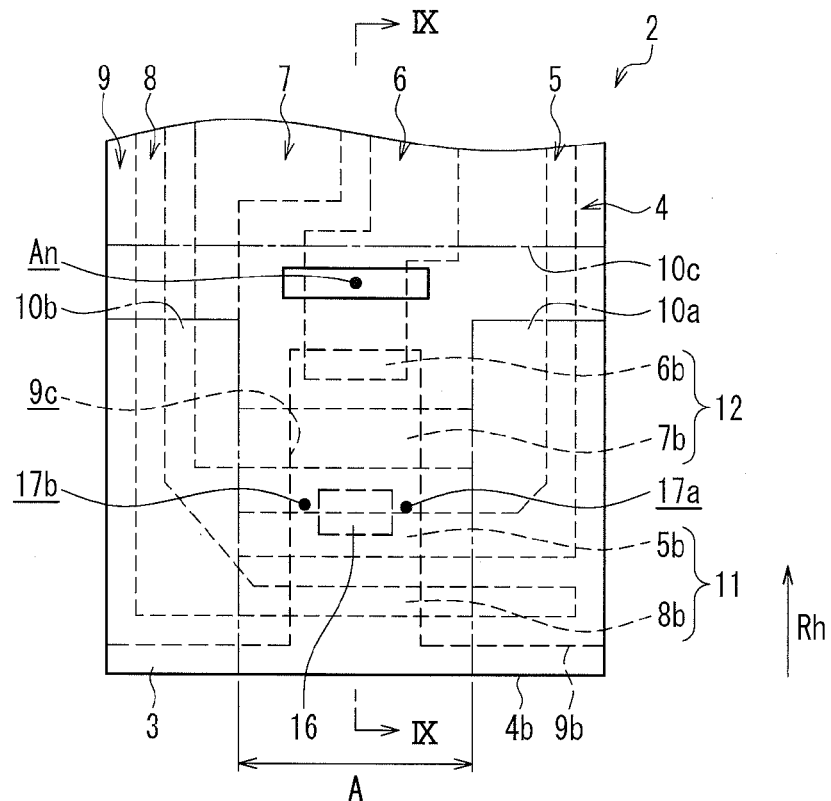
FIG. 8 is an enlarged plan view for explaining a portion of the analytical device shown in FIG. 7 on the side of a blood introduction hole.
Figure 9:
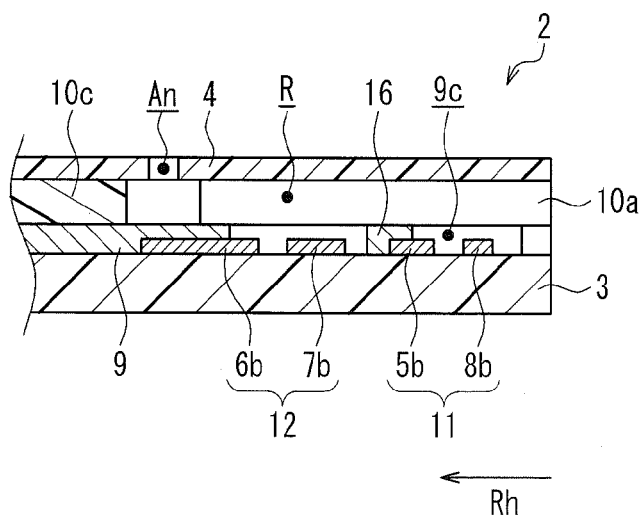
FIG. 9 is a cross-sectional view taken along line IX-IX in FIG. 8.
Figure 10:
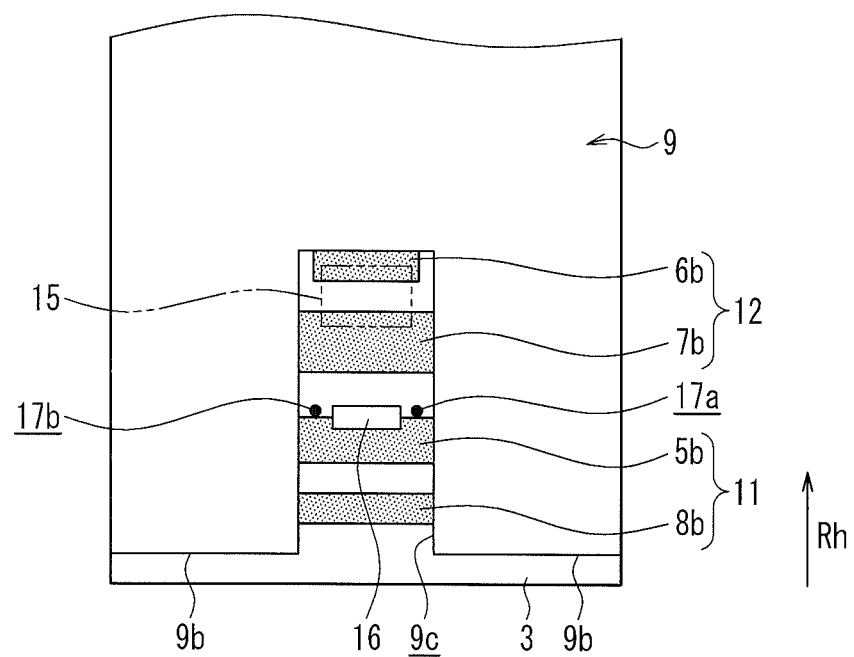
FIG. 10 is an enlarged plan view for explaining the configuration of a relevant portion of the analytical device shown in FIG. 7.

FIG. 7 is a plan view for explaining an analytical device according to a second embodiment of the invention. FIG. 8 is an enlarged plan view for explaining the configuration of a portion of the analytical device shown in FIG. 7 on the side of a blood introduction hole. FIG. 9 is a cross-sectional view taken along line IX-IX in FIG. 8. FIG. 10 is an enlarged plan view for explaining the configuration of a relevant portion of the analytical device shown in FIG. 7.

Referring to the drawings, this embodiment differs from the first embodiment mainly in that a dropped reagent restricting element is provided in a central portion with respect to the crosswise direction that crosses the inflow direction of blood, and two gaps are provided such that the dropped reagent restricting element is sandwiched between these two gaps. Note that like elements as those of the first embodiment are denoted by like reference numerals, and redundant descriptions thereof are omitted.

Specifically, as shown in FIG. 7, in the analytical device 2 of this embodiment, the signal lines 5, 6, 7, and 8 are formed on the substrate 3. The signal lines 5, 6, 7, and 8, like those of the first embodiment, include the linear wiring portions 5a, 6a, 7a, and 8a as well as the electrode portions 5b, 6b, 7b, and 8b that are provided at the left end portions of the corresponding signal lines 5, 6, 7, and 8 so as to be continuous with the respective wiring portions 5a, 6a, 7a, and 8a. However, unlike the wiring portions 5a, 6a, 7a, and 8a of the first embodiment, the wiring portions 5a, 6a, 7a, and 8a of this embodiment do not have the same width as shown in FIG. 7. Also, as shown in FIG. 8, in this embodiment, only the electrode portion 6b is formed substantially linearly with respect to the wiring portion 6a, so that a leading end portion of the electrode portion 6b is exposed in the cutout portion 9c.

Also, as shown in FIG. 7, unlike the cutout portion 9c of the first embodiment, the cutout portion 9c of this embodiment is configured so that the right end side of the cutout portion 9c opens. That is to say, in the cutout portion 9c of this embodiment, as shown in FIGS. 8 and 9, the introduction hole side of the flow path R opens. Thus, blood can be introduced more easily than in the first embodiment.

Also, as illustrated in FIG. 10, on the upstream side in the flow path R, the pair of hematocrit electrodes 11 are substantially constituted by those portions of the electrode portions 5b and 8b that are exposed in the cutout portion 9c. On the downstream side in the flow path R, the pair of glucose electrodes 12 are substantially constituted by those portions of the electrode portions 6b and 7b that are exposed in the cutout portion 9c. As shown by a chain double-dashed line in FIG. 10, the solidified dropped reagent 15 is placed on the pair of glucose electrodes 12.

Also, in the flow path R, as illustrated in FIG. 10, a dropped reagent restricting element 16 that restricts the movement of the dropped reagent 15 in a liquid state is provided between the downstream end portion of the pair of hematocrit electrodes 11 and the upstream end portion of the pair of glucose electrodes 12. This dropped reagent restricting element 16 is formed simultaneously with the resist ink (defining element) 9. As shown in FIG. 10, the dropped reagent restricting element 16 is formed on the electrode portion 5b of one of the pair of hematocrit electrodes 11. More specifically, a portion of the dropped reagent restricting element 16 is provided so as to be overlaid on a portion of the electrode portion 5b, and the other portion of the dropped reagent restricting element 16 is provided between the downstream end portion of the pair of hematocrit electrodes 11 and the upstream end portion of the pair of glucose electrodes 12.

Also, in the flow path R, as illustrated in FIG. 10, in the crosswise direction that crosses the inflow direction Rh of blood (e.g., orthogonal direction that is orthogonal to the inflow direction Rh), the dropped reagent restricting element 16 is provided in a central portion with respect to the crosswise direction, and two gaps 17a and 17b are provided such that the dropped reagent restricting element 16 is sandwiched between these two gaps 17a and 17b. That is to say, in the flow path R, the dropped reagent restricting element 16 is formed between the two gaps 17a and 17b.

With the above-described configuration, this embodiment can achieve the same effects as the first embodiment. Moreover, according to this embodiment, since the dropped reagent restricting element 16 is formed between the two gaps 17a and 17b in the flow path R, the amount of blood that is allowed to flow to the side of the pair of glucose electrodes 12 can be increased as compared with that of the first embodiment. Furthermore, according to this embodiment, since the dropped reagent restricting element 16 is provided in the central portion with respect to the crosswise direction that crosses the inflow direction Rh of blood, the movement of the dropped reagent 15 can be more reliably restricted. That is to say, the dropped reagent restricting element 16 can more reliably suppress the movement of the dropped reagent 15 to the side of the pair of hematocrit electrodes 11.

Third Embodiment

Figure 11:
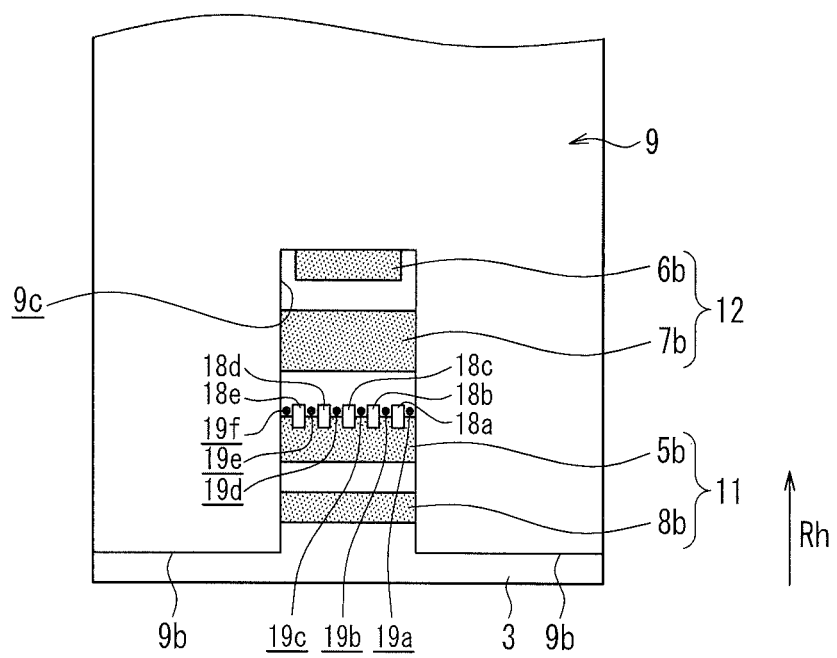
FIG. 11 is an enlarged plan view for explaining the configuration of a relevant portion of an analytical device according to a third embodiment of the invention.

FIG. 11 is an enlarged plan view for explaining the configuration of a relevant portion of an analytical device according to a third embodiment of the invention.

Referring to the drawings, this embodiment differs from the second embodiment mainly in that five dropped reagent restricting elements and six gaps are provided. Note that like elements as those of the second embodiment are denoted by like reference numerals, and redundant descriptions thereof are omitted.

Specifically, as illustrated in FIG. 11, in the analytical device of this embodiment, dropped reagent restricting elements 18a, 18b, 18c, 18d, and 18e that restrict the movement of the dropped reagent 15 in a liquid state are provided between the downstream end portion of the pair of hematocrit electrodes 11 and the upstream end portion of the pair of glucose electrodes 12 in the flow path R. These dropped reagent restricting elements 18a, 18b, 18c, 18d, and 18e are formed simultaneously with the resist ink (defining element) 9. As shown in FIG. 11, the dropped reagent restricting elements 18a, 18b, 18c, 18d, and 18e are formed on the electrode portion 5b of one of the pair of hematocrit electrodes 11. More specifically, a portion of each of the dropped reagent restricting elements 18a, 18b, 18c, 18d, and 18e is provided so as to be overlaid on a portion of the electrode portion 5b, and the other portion of each of the dropped reagent restricting elements 18a, 18b, 18c, 18d, and 18e is provided between the downstream end portion of the pair of hematocrit electrodes 11 and the upstream end portion of the pair of glucose electrodes 12. Note that the dropped reagent 15 placed on the pair of glucose electrodes 12 is omitted from FIG. 11 (the same omission applies to FIGS. 12 to 16, which will be described later).

Also, in the flow path R, as illustrated in FIG. 11, the dropped reagent restricting elements 18a, 18b, 18c, 18d, and 18e and six gaps 19a,19b, 19c, 19d, 19e, and 19f are provided in the crosswise direction that crosses the inflow direction Rh of blood (e.g., orthogonal direction that is orthogonal to the inflow direction Rh). That is to say, in the flow path R, the gaps 19a, 19b, 19c, 19d, 19e, and 19f are formed between adjacent two dropped reagent restricting elements of the dropped reagent restricting elements 18a, 18b, 18c, 18d, and 18e, between the dropped reagent restricting element 18a and the resist ink 9, and between the dropped reagent restricting element 18e and the resist ink 9.

With the above-described configuration, this embodiment can achieve the same effects as the second embodiment. Moreover, according to this embodiment, since the five dropped reagent restricting elements 18a, 18b, 18c, 18d, and 18e as well as the six gaps 19a, 19b, 19c, 19d, 19e, and 19f are arranged in a straight line, it is possible to increase the amount of blood that is allowed to flow to the side of the pair of glucose electrodes 12 while suppressing the movement of the dropped reagent 15 to the side of the pair of hematocrit electrodes 11.

Fourth Embodiment

Figure 12:
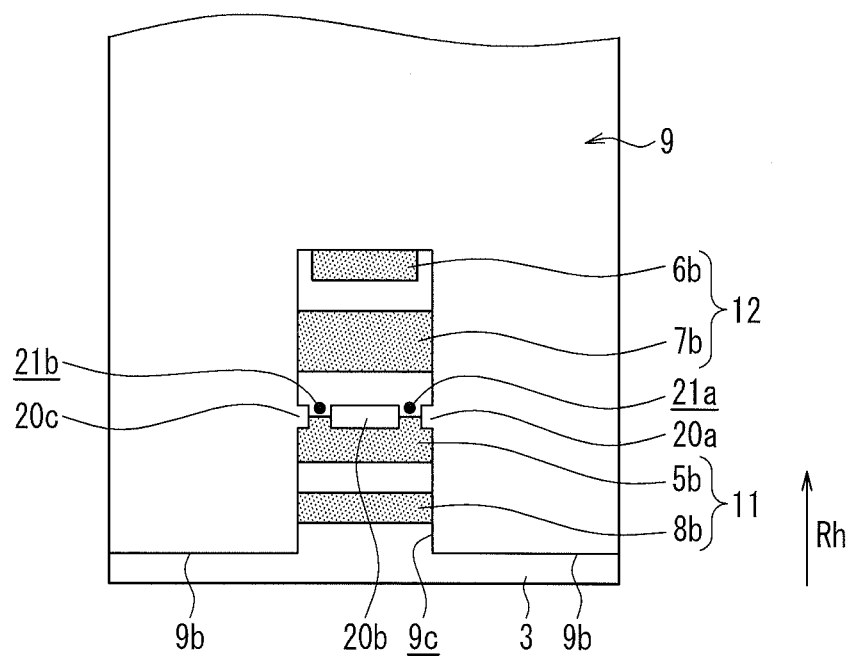
FIG. 12 is an enlarged plan view for explaining the configuration of a relevant portion of an analytical device according to a fourth embodiment of the invention.

FIG. 12 is an enlarged plan view for explaining the configuration of a relevant portion of an analytical device according to a fourth embodiment of the invention.

Referring to the drawings, this embodiment differs from the first embodiment mainly in that three dropped reagent restricting elements and two gaps are provided. Note that like elements as those of the first embodiment are denoted by like reference numerals, and redundant descriptions thereof are omitted.

Specifically, as illustrated in FIG. 12, in the analytical device of this embodiment, dropped reagent restricting elements 20a, 20b, and 20c that restrict the movement of the dropped reagent 15 in a liquid state are provided between the downstream end portion of the pair of hematocrit electrodes 11 and the upstream end portion of the pair of glucose electrodes 12 in the flow path R. These dropped reagent restricting elements 20a, 20b, and 20c are formed simultaneously with the resist ink (defining element) 9, and the dropped reagent restricting elements 20a and 20c are formed integrally with the resist ink 9. The dropped reagent restricting element 20b is provided in a central portion with respect to the crosswise direction that crosses the inflow direction Rh of blood. As shown in FIG. 11, the dropped reagent restricting elements 20a, 20b, and 20c are formed on the electrode portion 5b of one of the pair of hematocrit electrodes 11. More specifically, a portion of each of the dropped reagent restricting elements 20a, 20b, and 20c is provided so as to be overlaid on a portion of the electrode portion 5b, and the other portion of each of the dropped reagent restricting elements 20a, 20b, and 20c is provided between the downstream end portion of the pair of hematocrit electrodes 11 and the upstream end portion of the pair of glucose electrodes 12.

Also, in the flow path R, as illustrated in FIG. 12, the dropped reagent restricting elements 20a, 20b, and 20c as well as gaps 21a and 21b are provided in the crosswise direction that crosses the inflow direction Rh of blood (e.g., orthogonal direction that is orthogonal to the inflow direction Rh). That is to say, in the flow path R, the gap 21a is formed between the two dropped reagent restricting elements 20a and 20b, and the gap 21b is formed between the two dropped reagent restricting elements 20b and 20c.

With the above-described configuration, this embodiment can achieve the same effects as the first embodiment. Moreover, according to this embodiment, since the gap 21a is formed between the two dropped reagent restricting elements 20a and 20b, and the gap 21b is formed between the two dropped reagent restricting elements 20b and 20c, it is possible to more reliably suppress the movement of the dropped reagent 15 to the side of the pair of hematocrit electrodes 11 than in the first embodiment while allowing blood to flow to the side of the pair of glucose electrodes 12. The reason for this is that according to this embodiment, since the dropped reagent restricting element 20b is provided in the central portion with respect to the crosswise direction that crosses the inflow direction Rh of blood, movement of the dropped reagent 15 can be more reliably restricted.

Fifth Embodiment

Figure 13:
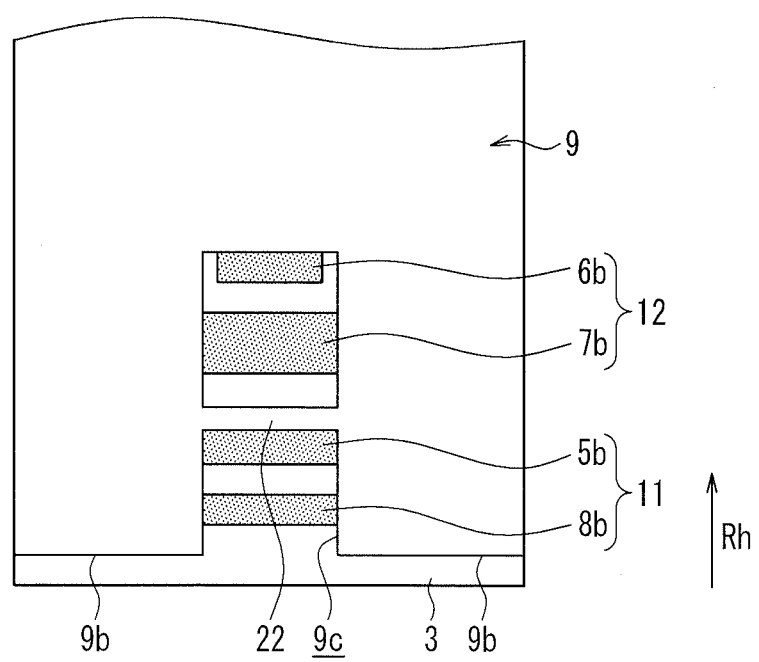
FIG. 13 is an enlarged plan view for explaining the configuration of a relevant portion of an analytical device according to a fifth embodiment of the invention.

FIG. 13 is an enlarged plan view for explaining the configuration of a relevant portion of an analytical device according to a fifth embodiment of the invention.

Referring to the drawings, this embodiment differs from the first embodiment mainly in that a dropped reagent restricting element is formed with no gap being created. Note that like elements as those of the first embodiment are denoted by like reference numerals, and redundant descriptions thereof are omitted.

Specifically, as illustrated in FIG. 13, in the analytical device of this embodiment, a dropped reagent restricting element 22 that restricts the movement of the dropped reagent 15 in a liquid state is provided between the downstream end portion of the pair of hematocrit electrodes 11 and the upstream end portion of the pair of glucose electrodes 12 in the flow path R. This dropped reagent restricting element 22 is formed integrally with the resist ink (defining element) 9. As shown in FIG. 13, the dropped reagent restricting element 22 is formed on the electrode portion 5b of one of the pair of hematocrit electrodes 11. More specifically, a portion of the dropped reagent restricting element 22 is provided so as to be overlaid on a portion of the electrode portion 5b, and the other portion of the dropped reagent restricting element 22 is provided between the downstream end portion of the pair of hematocrit electrodes 11 and the upstream end portion of the pair of glucose electrodes 12.

Also, in the analytical device of this embodiment, the dropped reagent restricting element 22 is provided such that the cutout portion 9c is divided by the dropped reagent restricting element 22. However, like the other embodiments, the dropped reagent restricting element 22 has the same thickness as the resist ink 9, and thus, in the flow path R, the space surrounded by the opposing substrate 4 and the double-sided adhesive tapes 10a and 10b enables blood to flow to the side of the pair of glucose electrodes 12 smoothly.

With the above-described configuration, this embodiment can achieve the same effects as the first embodiment. Moreover, according to this embodiment, the dropped reagent restricting element 22 can completely suppress the movement of the dropped reagent 15 to the side of the pair of hematocrit electrodes 11.

Sixth Embodiment

Figure 14:
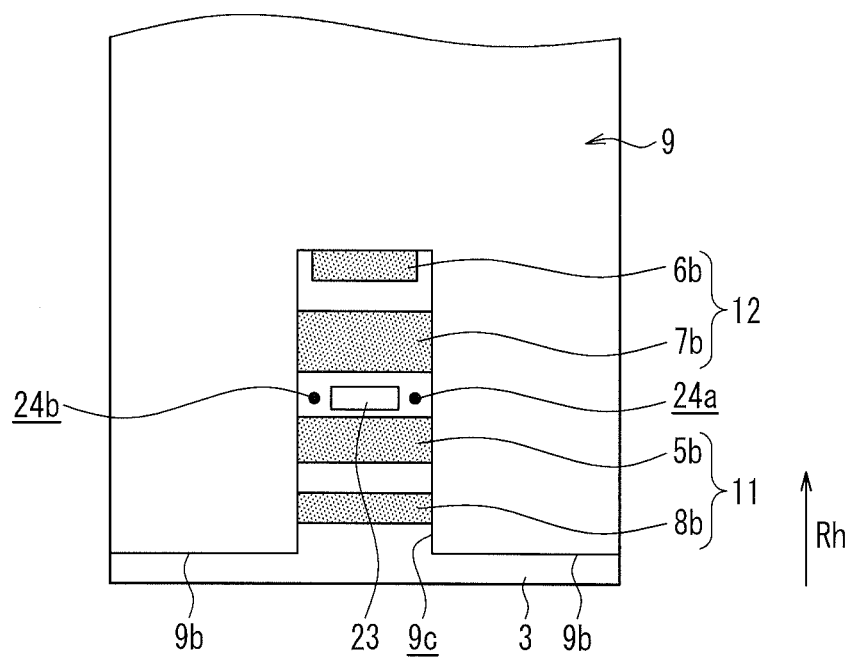
FIG. 14 is an enlarged plan view for explaining the configuration of a relevant portion of an analytical device according to a sixth embodiment of the invention.

FIG. 14 is an enlarged plan view for explaining the configuration of a relevant portion of an analytical device according to a sixth embodiment of the invention.

Referring to the drawings, this embodiment differs from the second embodiment mainly in that a dropped reagent restricting element is provided in a position at which the dropped reagent restricting element does not overlap the hematocrit electrodes. Note that like elements as those of the second embodiment are denoted by like reference numerals, and redundant descriptions thereof are omitted.

Specifically, as illustrated in FIG. 14, in the analytical device of this embodiment, a dropped reagent restricting element 23 that restricts the movement of the dropped reagent 15 in a liquid state is provided between the downstream end portion of the pair of hematocrit electrodes 11 and the upstream end portion of the pair of glucose electrodes 12 in the flow path R. This dropped reagent restricting element 23 is formed simultaneously with the resist ink (defining element) 9. As shown in FIG. 14, the dropped reagent restricting element 23 is formed between the electrode portion 5b of one of the pair of hematocrit electrodes 11 and the electrode portion 7b of one of the pair of glucose electrodes 12. More specifically, the dropped reagent restricting element 23, unlike the counterparts of the other embodiments, is provided so as not to be overlaid on any portion of the electrode portion 5b.

Also, in the flow path R, as illustrated in FIG. 14, in the crosswise direction that crosses the inflow direction Rh of blood (e.g., orthogonal direction that is orthogonal to the inflow direction Rh), the dropped reagent restricting element 23 is provided in a central portion with respect to the crosswise direction, and two gaps 24a and 24b are provided such that the dropped reagent restricting element 23 is sandwiched between these two gaps 24a and 24b. That is to say, in the flow path R, the dropped reagent restricting element 23 is formed between the two gaps 24a and 24b.

With the above-described configuration, this embodiment can achieve the same effects as the second embodiment. Moreover, according to this embodiment, since the two gaps 24a and 24b are formed in the flow path R such that the dropped reagent restricting element 23 is sandwiched between the gaps 24a and 24b, the amount of blood that is allowed to flow to the side of the pair of glucose electrodes 12 can be increased as compared with that of the first embodiment. Furthermore, according to this embodiment, since the dropped reagent restricting element 23 is provided in the central portion with respect to the crosswise direction that crosses the inflow direction Rh of blood, the movement of the dropped reagent 15 can be more reliably restricted. That is to say, the dropped reagent restricting element 23 can more reliably suppress the movement of the dropped reagent 15 to the side of the pair of hematocrit electrodes 11.

Seventh Embodiment

Figure 15:
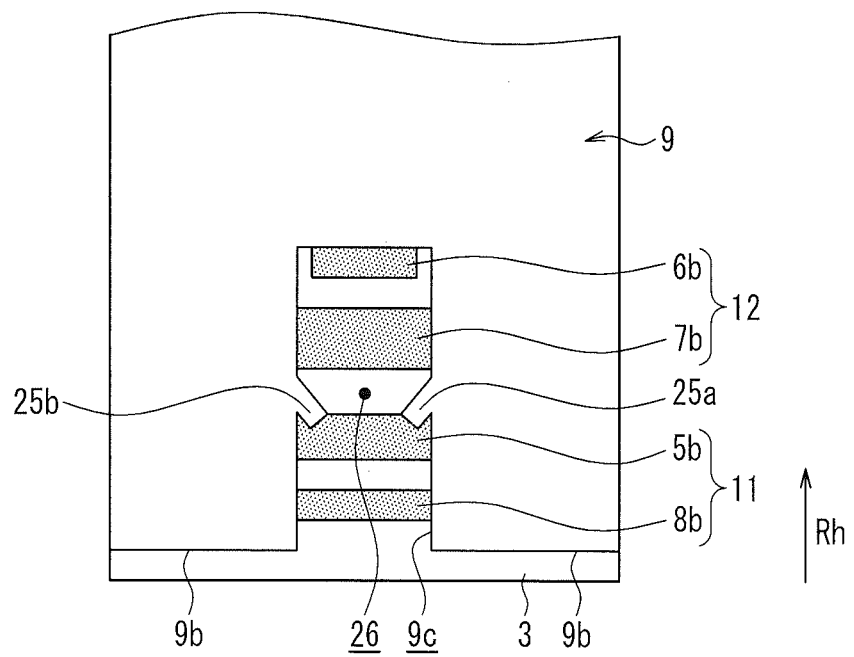
FIG. 15 is an enlarged plan view for explaining the configuration of a relevant portion of an analytical device according to a seventh embodiment of the invention.

FIG. 15 is an enlarged plan view for explaining the configuration of a relevant portion of an analytical device according to a seventh embodiment of the invention.

Referring to the drawings, this embodiment differs from the first embodiment mainly in that dropped reagent restricting elements that are inclined in the direction opposite to the inflow direction of blood are provided. Note that like elements as those of the first embodiment are denoted by like reference numerals, and redundant descriptions thereof are omitted.

Specifically, as illustrated in FIG. 15, in the analytical device of this embodiment, dropped reagent restricting elements 25a and 25b that restrict the movement of the dropped reagent 15 in a liquid state are provided between the downstream end portion of the pair of hematocrit electrodes 11 and the upstream end portion of the pair of glucose electrodes 12 in the flow path R. These dropped reagent restricting elements 25a and 25b are formed integrally with the resist ink (defining element) 9. As shown in FIG. 15, the dropped reagent restricting elements 25a and 25b are formed on the electrode portion 5b of one of the pair of hematocrit electrodes 11. More specifically, a portion of each of the dropped reagent restricting elements 25a and 25b is provided so as to be overlaid on a portion of the electrode portion 5b, and the other portion of each of the dropped reagent restricting elements 25a and 25b is provided between the downstream end portion of the pair of hematocrit electrodes 11 and the upstream end portion of the pair of glucose electrodes 12. Furthermore, the dropped reagent restricting elements 25a and 25b are formed in a state in which the dropped reagent restricting elements 25a and 25b are inclined in the direction opposite to the inflow direction Rh of blood such that leading end portions of the respective dropped reagent restricting elements 25a and 25b protrude to the side of the pair of hematocrit electrodes 11.

Also, in the flow path R, as illustrated in FIG. 15, in the crosswise direction that crosses the inflow direction Rh of blood (e.g., orthogonal direction that is orthogonal to the inflow direction Rh), the dropped reagent restricting elements 25a and 25b as well as a gap 26 are provided. That is to say, in the flow path R, the gap 26 is formed between the two dropped reagent restricting elements 25a and 25b.

With the above-described configuration, this embodiment can achieve the same effects as the first embodiment. Moreover, according to this embodiment, since the dropped reagent restricting elements 25a and 25b are formed in a state in which the dropped reagent restricting elements 25a and 25b are inclined in the direction opposite to the inflow direction Rh of blood, the reagent 15 can be easily dropped on the pair of glucose electrodes 12.

Eighth Embodiment

Figure 16:
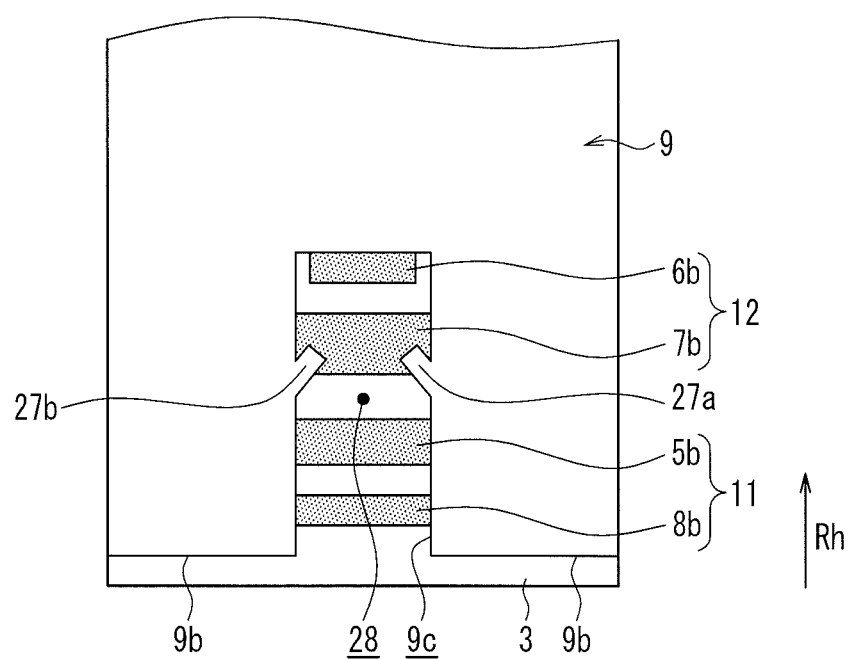
FIG. 16 is an enlarged plan view for explaining the configuration of a relevant portion of an analytical device according to an eighth embodiment of the invention.

FIG. 16 is an enlarged plan view for explaining the configuration of a relevant portion of an analytical device according to an eighth embodiment of the invention.

Referring to the drawings, this embodiment differs from the first embodiment mainly in that dropped reagent restricting elements that are inclined in the inflow direction of blood are provided. Note that like elements as those of the first embodiment are denoted by like reference numerals, and redundant descriptions thereof are omitted.

Specifically, as illustrated in FIG. 16, in the analytical device of this embodiment, dropped reagent restricting elements 27a and 27h that restrict the movement of the dropped reagent 15 in a liquid state are provided between the downstream end portion of the pair of hematocrit electrodes 11 and the upstream end portion of the pair of glucose electrodes 12 in the flow path R. These dropped reagent restricting elements 27a and 27h are formed integrally with the resist ink (defining element) 9. As shown in FIG. 16, these dropped reagent restricting elements 27a and 27h are formed on the electrode portion 7b of one of the pair of glucose electrodes 12. More specifically, a portion of each of the dropped reagent restricting elements 27a and 27b is provided so as to be overlaid on a portion of the electrode portion 7b, and the other portion of each of the dropped reagent restricting elements 27a and 27h is provided between the downstream end portion of the pair of hematocrit electrodes 11 and the upstream end portion of the pair of glucose electrodes 12. Furthermore, the dropped reagent restricting elements 27a and 27h are formed in a state in which the dropped reagent restricting elements 27a and 27h are inclined in the inflow direction Rh of blood such that leading end portions of the dropped reagent restricting elements 27a and 27h protrude to the side of the pair of glucose electrodes 12.

Also, in the flow path R, as illustrated in FIG. 16, in the crosswise direction that crosses the inflow direction Rh of blood (e.g., orthogonal direction that is orthogonal to the inflow direction Rh), the dropped reagent restricting elements 27a and 27b as well as a gap 28 are provided. That is to say, in the flow path R, the gap 28 is formed between the two dropped reagent restricting elements 27a and 27b.

With the above-described configuration, this embodiment can achieve the same effects as the first embodiment. Moreover, according to this embodiment, since the dropped reagent restricting elements 27a and 27h are formed in a state in which the dropped reagent restricting elements 27a and 27b are inclined in the inflow direction Rh of blood, the amount of blood that is allowed to flow to the side of the pair of glucose electrodes 12 can be increased as compared with that of the first embodiment.

The embodiments described above are to be considered in all respects as illustrative and not restrictive. The scope of the invention is indicated by the appended claims rather than by the foregoing description, and all changes which come within the meaning and range of equivalency of the claims are therefore intended to be embraced therein.

For example, in the foregoing description, a case where a blood glucose meter is used as the measuring apparatus has been described. However, the invention is not limited to this, and other measuring apparatuses for measuring, for example, the lactic acid level or the like from a sample (specimen) may also be used.

Also, in the description of the first to fifth, seventh, and eighth embodiments, a configuration in which a dropped reagent restricting element is provided on the electrode portion of one of the pair of hematocrit electrodes (first pair of electrodes) has been described. However, the invention is not limited to this, and a configuration may also be adopted in which a dropped reagent restricting element is provided on all the electrode portions (i.e., one and the other electrode portions) of the first pair of electrodes.

Also, in the description of the first to fifth, seventh, and eighth embodiments, a configuration in which a dropped reagent restricting element is provided on the pair of hematocrit electrodes (first pair of electrodes) has been described. However, the dropped reagent restricting element of the invention is not limited to this, and it is sufficient if a dropped reagent restricting element is formed in a position that is different from the middle position between the first pair of electrodes and the second pair of electrodes and that is shifted to the side of either one pair of the first pair of electrodes and the second pair of electrodes. Preferably, as described in the first to fifth, seventh, and eighth embodiments, it is sufficient if a dropped reagent restricting element is formed on either one pair of the first pair of electrodes and the second pair of electrodes. Thus, a sufficient amount of reagent can be dropped on the other pair of the first pair of electrodes and the second pair of electrodes. In addition, other than the explanation mentioned above, the dropped reagent restricting element is formed on both of the first pair of electrodes and the second pair of electrodes. That is, the dropped reagent restricting element of the invention is formed on at least one of the first pair of electrodes and the second pair of electrodes.

Also, in the foregoing description, a configuration in which a pair of hematocrit electrodes are used as the first pair of electrodes on the upstream side in the flow path, and a pair of glucose electrodes are used as the second pair of electrodes on the downstream side in the flow path has been described. However, the invention is not limited to this, and it it also possible to use a pair of glucose electrodes as the first pair of electrodes and a pair of hematocrit electrodes as the second pair of electrodes. In this case, it is preferable to provide the dropped reagent restricting element on the pair of hematocrit electrodes as well; however, the dropped reagent restricting element may also be provided on the pair of glucose electrodes.

Also, in the foregoing description, a case where the first electrode pair forming step, the second electrode pair forming step, and the dropped reagent restricting element forming step are completed at the same time has been described. However, there is no limitation to the method for manufacturing the analytical device of the invention as long as the method includes the first electrode pair forming step, the second electrode pair forming step, and the dropped reagent restricting element forming step. For example, the dropped reagent restricting element forming step may also be performed after the first and second pairs of electrodes are formed in corresponding positions within the cutout portion of the resist ink (defining element).

Also, in the foregoing description, a case where a reagent is dropped on the second pair of electrodes has been described. However, the dropped reagent of the invention is not limited to this. A configuration in which a reagent is dropped on at least one pair of the first and second pairs of electrodes may also be adopted. A configuration in which two different types of reagents are dropped on the first and second pairs of electrodes, respectively, and a configuration in which the same reagent is dropped on both of the first and second pairs of electrodes may also be adopted.

The invention is useful for an analytical device that allows a sample to sufficiently reach as far as a second pair of electrodes that are provided on the downstream side in a flow path, a method for manufacturing the analytical device, and a measuring apparatus using the analytical device.

Also, the invention is useful for an analytical device that allows a sufficient amount of reagent to be dropped on a pair of electrodes, a method for manufacturing the analytical device, and a measuring apparatus using the analytical device.

What is claimed is:

1. An analytical device comprising:
a substrate;
a defining element defining a flow path of a sample;
a first pair of electrodes formed on the substrate and located in the flow path;
a second pair of electrodes formed on the substrate and located downstream of the first pair of electrodes in the flow path; and
a dropped reagent restricting element formed so that the dropped reagent restricting element overlaps with at least one electrode of the first pair or at least one electrode of the second pair of electrodes or alternatively, with at least one electrode of the first pair and at least one electrode of the second pair of electrodes, the dropped reagent restricting element restricting movement of a dropped reagent, wherein:

the dropped reagent is on the second pair of electrodes but not on the first pair of electrodes, or the dropped reagent is on the second pair of electrodes and a different dropped reagent is on the first pair of electrodes;

the dropped reagent restricting element and two gaps are positioned on a common axis which is perpendicular to an inflow direction Rh of the sample; and the two gaps are in a plane which is parallel to the surface of the substrate having the flow path and are provided one on each side of the dropped reagent restricting element is sandwiched between the two gaps.

2. The analytical device according to claim 1, wherein the dropped reagent restricting element is formed on one of the first pair of electrodes or on one of the second pair of electrodes.

3. The analytical device according to claim 1, wherein the dropped reagent is on the second pair of electrodes, and the dropped reagent restricting element is formed on one of the first pair of electrodes.

4. The analytical device according to claim 1, wherein the dropped reagent restricting element is formed integrally with a portion of the defining element.

5. The analytical device according to claim 1, wherein the dropped reagent restricting element is an insulator.

6. The analytical device according to claim 1, further comprising:

an opposing substrate that is provided opposite the substrate; and an adhesive layer for adhering the substrate and the opposing substrate to each other, wherein the defining element comprises an insulator provided on the substrate, the adhesive layer, and the opposing substrate.

7. The analytical device according to claim 6, wherein a vent communicating with the flow path is provided in the opposing substrate.

8. The analytical device according to claim 1, wherein the dropped reagent restricting element is formed on one of the first pair of electrodes and on one of the second pair of electrodes.

9. The analytical device according to claim 1, wherein the sample is blood.

10. The analytical device according to claim 1, wherein the defining element is a resist ink.

11. The analytical device according to claim 10, wherein the resist ink is a thermosetting ink.

12. A measuring apparatus comprising the analytical device according to claim 1.

13. The measuring apparatus according to claim 12, further comprising a blood glucose meter.

14. An analytical device comprising:

a substrate;

a defining element defining a flow path of a sample;

a first pair of electrodes formed on the substrate and located in the flow path;

a second pair of electrodes formed on the substrate and located downstream of the first pair of electrodes in the flow path; and a dropped reagent restricting element formed so that there is no overlap between the dropped reagent restricting element and the first pair or the second pair of electrodes, the dropped reagent restricting element restricting movement of a dropped reagent, wherein:

the dropped reagent is on the second pair of electrodes but not on the first pair of electrodes, or the dropped reagent is on the second pair of electrodes and a different dropped reagent is on the first pair of electrodes, the dropped reagent restricting element and two gaps are positioned on a common axis which is perpendicular to an inflow direction Rh of the sample; and the two gaps are in a plane which is parallel to the surface of the substrate having the flow path and are provided one on each side of the dropped reagent restricting element is sandwiched between the two gaps.

15. A method for manufacturing an analytical device comprising:

a substrate, a defining element defining a flow path of a sample, a first pair of electrodes, and a second pair of electrodes, the method comprising:

a step of forming the first pair of electrodes in the flow path on the substrate, where one of the electrodes of the first pair of electrodes is downstream of the other electrode of the first pair of electrodes;

a step of forming the second pair of electrodes downstream of the first pair of electrodes in the flow path on the substrate;

a step of forming a dropped reagent restricting element so that there is no overlap between the dropped reagent restricting element and the first pair or the second pair of electrodes, or so that the dropped reagent restricting element overlaps with at least one electrode of the first pair or at least one electrode of the second pair of electrodes or alternatively, with at least one electrode of the first pair and at least one electrode of the second pair of electrodes, where the dropped reagent restricting element is positioned in the flow path such that two gaps are created on a common axis which is perpendicular to an inflow direction of the sample, and where the dropped reagent restricting element restricts movement of a dropped reagent; and a step of dropping the dropped reagent on the second pair of electrodes but not on the first pair of electrodes, or dropping the dropped reagent on the second pair of electrodes and a dropping a different dropped reagent on the first pair of electrodes; and wherein the two gaps are in a plane which is parallel to the surface of the substrate having the flow path and are provided one on each side of the dropped reagent restricting element such that the dropped reagent restricting element is sandwiched between the two gaps.

16. The method for manufacturing an analytical device according to claim 15, wherein in the dropped reagent restricting element forming step, the dropped reagent restricting element is formed on one of the first pair of electrodes and one of the second pair of electrodes.

17. The method according to claim 15, wherein in the dropped reagent restricting element forming step, the dropped reagent restricting element is formed on one of the first pair of electrodes or on one of the second pair of electrodes.

18. The method according to claim 15,
wherein in the dropped reagent restricting element forming step, there is no overlap between the dropped reagent restricting element and the first pair or the second pair of electrodes.

* * * * *